United States Patent
Pacioretty et al.

(12) 
(10) Patent No.: US 6,733,793 B2
(45) Date of Patent: May 11, 2004

(54) ORAL COMPOSITION WITH INSULIN-LIKE ACTIVITIES AND METHODS OF USE

(75) Inventors: Linda M. Pacioretty, Brooktondale, NY (US); John G. Babish, Brooktondale, NY (US)

(73) Assignee: MetaProteomics, LLC, San Clemente, CA (US)

(*) Notice: Subject to any disclaimer, the term of this patent is extended or adjusted under 35 U.S.C. 154(b) by 14 days.

(21) Appl. No.: 10/163,254

(22) Filed: Jun. 4, 2002

(65) Prior Publication Data
US 2003/0224061 A1 Dec. 4, 2003

(51) Int. Cl.$^7$ .................. A61K 33/24; A61K 33/26; A61K 31/385; A61K 31/205; A61K 31/185
(52) U.S. Cl. .............. 424/646; 514/2; 514/12; 514/21; 514/440; 514/547; 514/556; 514/561; 514/578; 514/866; 514/904; 514/905; 514/909; 424/725; 424/780; 424/195.15; 424/195.16; 424/195.17; 426/2; 426/72; 426/74
(58) Field of Search .................. 424/646, 725, 424/780, 195.15, 195.16, 195.17; 514/440, 556, 561, 578, 866, 909, 2, 12, 21, 547, 904, 905; 426/2, 72, 74

(56) References Cited

U.S. PATENT DOCUMENTS

| | | | |
|---|---|---|---|
| 4,751,085 A | 6/1988 | Gaull | 424/643 |
| 5,550,113 A | 8/1996 | Mann | 514/54 |
| 5,599,835 A | 2/1997 | Fischer | 514/440 |
| 5,614,224 A | 3/1997 | Womack | 424/646 |
| 5,693,664 A | 12/1997 | Wessel et al. | 514/440 |
| 5,730,988 A | 3/1998 | Womack | 424/774 |
| 5,885,980 A | 3/1999 | Gutierrez et al. | 514/186 |
| 5,888,993 A | 3/1999 | McNeil et al. | 514/186 |

FOREIGN PATENT DOCUMENTS

WO    WO 00/72854 A1    12/2000

OTHER PUBLICATIONS

M. Elchebly, et al., "Increased Insulin Sensitivity and Obesity Resistance in Mice Lacking the Protein Tyrosine Phosphatase–1B Gene," Science, vol. 283, Mar. 5, 1999, pp. 1544–1548.

Primary Examiner—John Pak
(74) Attorney, Agent, or Firm—McDermott, Will & Emery

(57) ABSTRACT

An orally administered, novel dietary supplement or therapeutic composition capable of insulin-like activity in animals, preferably humans, is provided. Contained in the composition are therapeutically effective amounts of vanadyl sulfate, alpha-lipoic acid, taurine, and chromium carnitine. The composition is preferably orally administered on a daily basis for at least about 4 weeks and can be used by normal, healthy individuals as well as diabetics.

22 Claims, 1 Drawing Sheet

ORAL COMPOSITION WITH INSULIN-LIKE ACTIVITIES AND METHODS OF USE

FIELD OF THE INVENTION

The present invention relates to a composition of vanadyl sulfate, alpha-lipoic acid, taurine and chromium carnitine to augment or normalize cellular tyrosine phosphorylation responses to insulin, thereby normalizing insulin activity, decreasing catabolic activity in the diabetic state, decreasing serum lipoproteins and maintaining normal body weight in healthy humans and animals.

BACKGROUND OF THE INVENTION

The actions of insulin are initiated by its binding to insulin receptor, a disulfide-bonded heterotetrameric membrane protein (FIG. 1). Insulin binding causes conformational changes in insulin receptor that lead to autophosphorylation of the receptor and activation of the receptor's intrinsic tyrosine kinase activity. The function of the tyrosine kinase of insulin receptor is essential for the biological effects of insulin. After autophosphorylation, the insulin receptor can phosphorylate the tyrosine residues of several substrates, including the insulin receptor substrate (IRS) proteins, which in turn can activate downstream signaling molecules in hepatic, muscle and fat cells.

A protein tyrosine phosphatase termed PTP-1B can terminate the signaling cascade initiated by insulin by removing the phosphate from the insulin receptor. Studies indicate that increased expression of PTP-1B in mice gives rise to a form of insulin resistance termed type 2 non-insulin dependent diabetes mellitus (NIDDM). NIDDM is a complex disease characterized by progressive development of insulin resistance and defects in insulin secretion, which often leads to overt hyperglycemia. On the other hand, some data indicate that mice lacking the PTP-1 B gene are more sensitive to insulin's blood glucose-lowering effects than are control animals, and, these PTP-1B defective mice appear to be more resistant to weight gain when consuming a high-fat diet {Elchebly et al., 238 SCIENCE 1544–1548 (1999)].

Vanadate is known to be an inhibitor of many phosphatases. Some researchers have proposed that vanadate administration may mimic the activity of insulin. For example, U.S. Pat. No. 5,550,113 and U.S. Pat. No. 5,888,993 disclose vanadium salts for blood sugar regulation. U.S. Pat. No. 5,885,980 and U.S. Pat. No. 5,614,224 disclose vanadium salts for the treatment of diabetes.

However, vanadyl sulfate is not widely used to mimic the activity of insulin because chronic administration of vanadate can be toxic. Vanadyl sulfate has been shown to induce chromosomal damage and mitotic recombination in the fruit fly. Vanadyl sulfate can induce pulmonary inflammation in rats when inhaled. In vitro studies of bovine papilloma virus DNA-tranfected C3H/10T1/2 cells have demonstrated that vanadyl sulfate possess tumor promotion activity.

To avoid the toxic build-up of vanadate, some researchers suggest administering it intermittently. For example, U.S. Pat. No. 5,730,988 to Womack (Mar. 24, 1998) discloses administration of nutritional supplements containing a source of vanadate in a "Phase I" supplementation program and lipoic acid and *Gymnema sylvesire* in a "Phase II" supplementation cycle.

Given the potential usefulness of vanadyl sulfate in the treatment of diabetes, it would be desirable to administer compositions containing vanadyl sulfate to diabetic patients, and to normal individuals wishing to minimize their risk of developing NIDDM, if the undesirable side effects of vanadate could be avoided.

Alpha-lipoic acid has been studied as a potential treatment for improving glucose metabolism. U.S. Pat. No. 5,693,664 to Wessel et al. (Dec. 2, 1997) discloses the R-(+) enantiomer of alpha-lipoic acid and its metabolites for the treatment of diabetes. A formulation of DL-lipoic acid is described in U.S. Pat. No. 5,599,835 to Fischer (Feb. 4, 1997) for treatment of a metabolic aberration of the multienzyme complex of pyruvate dehydrogenase, which is symptomatic of diabetes mellitus.

Taurine is a conditionally essential amino acid that is found in the tissues of most animal species. It is not incorporated into proteins, but is found free in many tissues. Taurine is involved in a number of physiological processes including bile acid conjugation, osmoregulation, detoxification of xenobiotics, cell membrane stabilization, modulation of cellular calcium flux, and modulation of neuronal excitability. Low levels of taurine have been associated with retinal degeneration, growth retardation, and cardiomyopathy. Taurine has been used clinically in the treatment of cardiovascular diseases, hypercholesterolemia, seizure disorders, ocular disorders, diabetes, Alzheimer's disease, hepatic disorders, cystic fibrosis, and alcoholism. Animal and human studies indicate that taurine supplementation is effective in alleviating some of the complications of insulin-dependant diabetes. Taurine has been found to influence blood glucose and insulin levels, as well as increasing glycogen synthesis, and it may also be involved in the functioning and integrity of pancreatic beta cells.

Trivalent chromium is an essential trace element for normal carbohydrate metabolism and insulin sensitivity. Because of this biological activity, chromium supplementation has been studied as a potential therapy of insulin resistant states and dyslipidemias, and has been promoted as a health aid to the general population. Chromium has principally been studied for its possible benefits in improving blood sugar control in diabetic patients.

Chromium improves the glucose/insulin system in subjects with hypoglycemia, hyperglycemia, diabetes and hyperlipemia with no detectable effects on control subjects. Chromium improves insulin binding, insulin receptor number, insulin internalization, beta cell sensitivity and insulin receptor enzymes with overall increases in insulin sensitivity. There have been several studies involving chromium supplementation of subjects with NIDDM and/or lipemia and most have reported beneficial effects of chromium on the glucose/insulin system. In summary, chromium is involved in the control of the glucose/insulin system and the form of chromium is critical when evaluating the role of chromium in this system.

Several forms of chromium have been studied with respect to glucose metabolism and impact on insulin resistance. Controversy exists as to which supplemental form of chromium is preferable; and, regarding insulin resistance, this controversy is likely to continue. The present invention provides a novel composition of chromium (+3) as chromium carnitine. This chelated form of chromium, administered in combination with vanadyl sulfate, lipoic acid, and taurine, functions coordinately to normalizes insulin signaling in liver, muscle and fat cells.

Hence, while certain compounds are thought to separately mimic some of the activities of insulin, a single non-toxic composition that provides a more complete range of insulin-like activities would be desirable. The ideal formulation would (i) increase cell sensitivity to insulin, (ii) maintain normal serum glucose, (iii) decrease hypertriglyceridemia and/or lipoproteins, and (iv) maintain normal body weight even with consumption of a high fat diet. These objects and other are achieved in the present invention.

SUMMARY OF THE INVENTION

In accordance with the present invention, an oral formulation is provided that comprises vanadyl sulfate, alpha-lipoic acid, taurine and chromium carnitine. The present supplement; (a) increases cell sensitivity to insulin, (b) maintains normal serum glucose, (c) decreases serum triglycerides and/or serum lipoproteins, and (d) maintains normal body weight even with consumption of a high fat diet. The supplement can be used by normal, healthy individuals as well as diabetics.

The present invention also provides a method of oral supplementation in animals that includes administering to an animal suffering symptoms of diabetes a composition including therapeutically effective amounts of vanadyl sulfate, alpha-lipoic acid, taurine and chromium carnitine and continuing administration of the composition until the symptoms are reduced.

The present invention further provides a method of oral supplementation in animals that includes administering to an animal a composition, which includes therapeutically effective amounts of vanadyl sulfate, alpha-lipoic acid, taurine and chromium carnitine, and continuing administration of the composition until normalization of serum glucose is achieved.

The present invention still further provides a method of oral supplementation in animals that includes administering to an animal a composition, which includes therapeutically effective amounts of vanadyl sulfate, alpha-lipoic acid, taurine and chromium carnitine, and continuing administration of the composition until normalization of serum triglycerides or lipoproteins is achieved.

The present invention additionally provides a method of treating obesity in an animal that includes administering to an animal a composition including therapeutically effective amounts of vanadyl sulfate, alpha-lipoic acid, taurine and chromium carnitine.

According to the present invention, the animal is a mammal selected from the group consisting of humans, nonhuman primates, dogs, cats, horses or cattle.

A pharmaceutically acceptable carrier may also be used in the present compositions and formulations. The formulations can be manufactured in any form known to the skilled artisan, for example as solid capsules, caplets, softgels, liquids, bars, or functional foods.

Other features and advantages of the invention will become apparent from the following detailed description, taken in conjunction with the accompanying drawings, which illustrate, by way of example, the features of the invention.

DETAILED DESCRIPTION OF THE INVENTION

Figure 1:
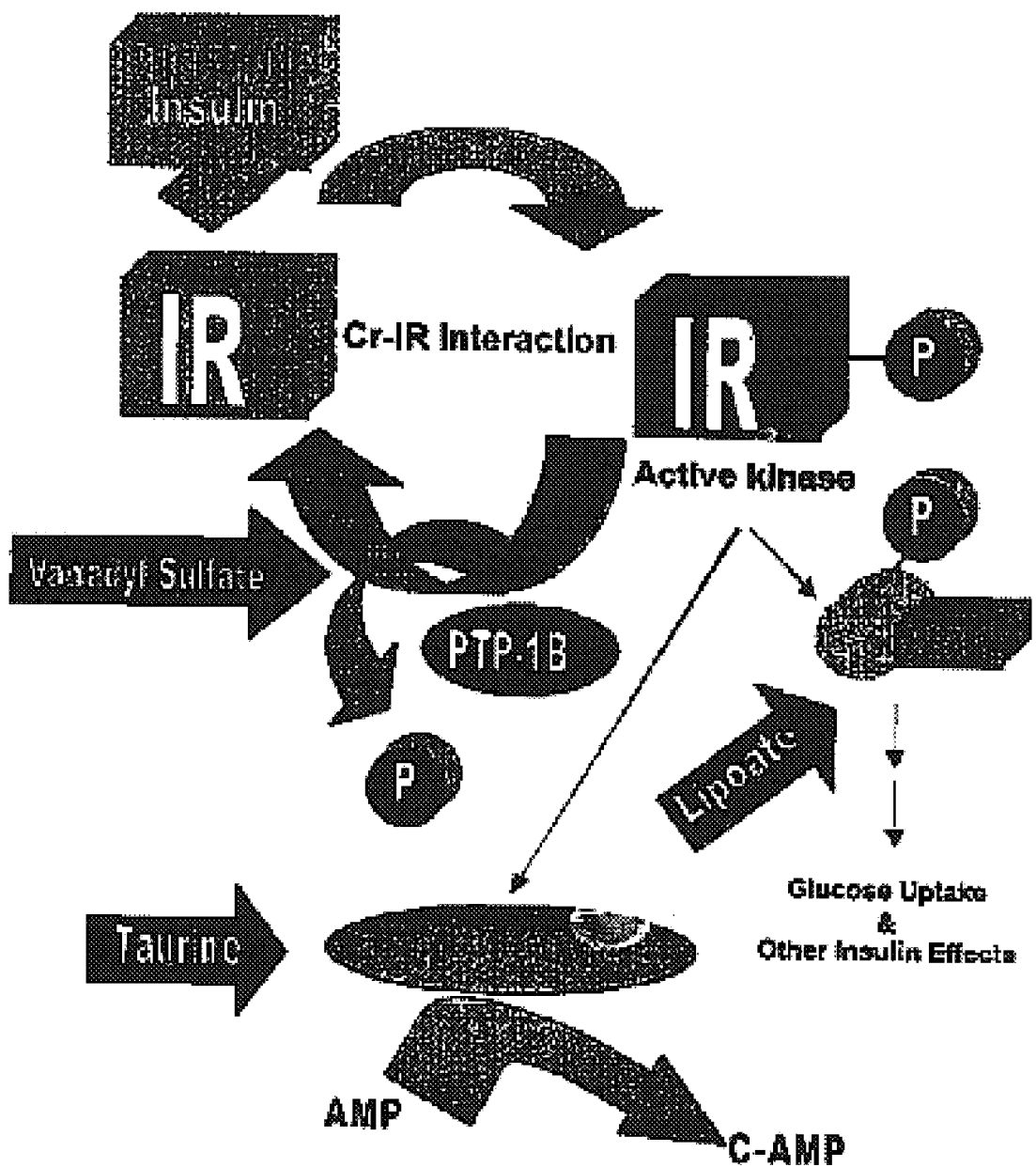
FIG. 1 provides a schematic diagram illustrating, according to the present invention, how the components of the present formulation, vanadyl sulfate, alpha-lipoic acid, taurine and chromium from chromium carnitine, can act together to enhance, augment or spare the effect of insulin on liver, muscle or fat cells. As illustrated, the tyrosine kinase signaling pathway is initiated through the interaction of insulin and the insulin receptor (IR), complexed with chromium, leading to the phosphorylation of insulin receptor. PTP-1B can remove the phosphate from insulin receptor, thereby inactivating its kinase activity. Vanadyl sulfate cam block the activity of phosphatases like PTP-1B, thereby preventing the dephosphorylation of insulin receptor. Taurine can activate cyclic AMP. Alpha-lipoic acid (Lipoate) can augment glucose uptake and lower serum lipid levels. The result is that this novel combination of ingredients enhances, augments or spares the effect of insulin on liver, muscle and/or fat cells.

Before the present composition and methods of making and using thereof are disclosed and described, it is to be understood that this invention is not limited to the particular configurations, as process steps and materials may vary somewhat. It is also intended to be understood that the terminology employed herein is used for the purpose of describing particular embodiments only and is not intended to be limiting since the scope of the present invention will be limited only by the appended claims and equivalents thereof. It must be noted that, as used in this specification and the appended claims, the singular forms "a," "an," and "the" include plural referents unless the context clearly dictates otherwise.

The present invention provides a composition that can be administered orally and includes vanadyl sulfate, alpha-lipoic acid, taurine and chromium carnitine. Each of these individual components affects the insulin-induced chain of activities to some degree. In combination, the resulting dietary supplement addresses the decreased insulin sensitivity and secondary pathologies associated with diabetes, normal aging and with NIDDM.

According to the present invention, compounds that inhibit PTP-1B can be used to prevent and treat obesity and diabetes. Vanadyl sulfate can inhibit PTP-1B but its toxicity prevents chronic administration and widespread acceptance. However, when combined with other compounds that have insulin-like activities, vanadyl sulfate can be used in such small dosages that it will not be toxic.

In another embodiment, the present composition works synergistically to enhance signaling by stimulating PI-3k with alpha-lipoic acid and by increasing the amount of phosphorylated IRS-1 with vanadyl sulfate, which maintains high levels of insulin receptor kinase activity (see FIG. 1). Attacking the insulin-activated cascade of events in at two different places by administering by vanadyl sulfate and alpha-lipoic acid, permits administration of lower dosages of vanadyl sulfate, thereby reducing the potential for adverse side effects.

Moreover, according to the present invention, the combination of vanadyl sulfate, alpha-lipoic acid, taurine and chromium carnitine works synergistically to mimic not only insulin's glucose-normalizing properties but also insulin's lipid-lowering properties. As seen in FIG. 1, the activation of the phosphodiesterase and production of c-AMP is independent of the tyrosine phosphorylation of IRS-1 and subsequent PI-3k activation. Thus, taurine and its effect on c-AMP provide synergistic lowering of lipids when combined with vanadyl sulfate, alpha-lipoic acid and chromium as chromium carnitine.

The current invention is designed to normalize insulin action in both glucose tolerance and weight management. In these regards, the current invention may be consumed by healthy persons wishing to prevent (a) developing NIDDM, (b) exhibiting high serum lipoprotein levels and (c) gaining weight on high fat diets.

The combination of vanadyl sulfate, lipoic acid, taurine and chromium carnitine suggested by the present invention is unique; (a) it provides a dietary formulation for the maintenence of normal insulin action at the insulin receptor that can be consumed by healthy persons as well as diabetics; (b) it can be taken orally; (c) it maintains its insulin-sparing activity over many months; (d) it normalizes serum glucose levels; (e) it normalizes serum lipoprotein levels; (f) it is safe over long periods of time; (g) it can be used to maintain normal body weight on high-fat diets; and (h) it can be cost-effective. Manufacturing and sale of this formulation should comply with all government regulations.

Vanadyl sulfate, alpha-lipoic acid, taurine and chromium carnitine can be obtained commercially, for example, as pharmaceutical grade preparations with a purity of greater than 95% by weight. Vanadyl sulfate can be purchased from Spectrum Chemicals MFG, Corp (Gardena, Calif.). Alpha-lipoic acid can be obtained from Technical Sourcing International, (Missoula, Mont.) and taurine can be obtained from Premium Ingredients, Ltd. Chromium carnitine can be obtained from Albion Laboratories (Clearfield, Utah). The currently proposed formulation of these four agents does not exist commercially.

The composition of this invention will contain "therapeutically effective amounts" of vanadyl sulfate, alpha-lipoic acid, taurine and chromium carnitine. As toted herein with respect to these components, "therapeutically effective amount" refers to that amount of the component that will contribute to the insulin-like activity of the composition. Preferably, the composition of this invention contains: (a) from about 0.08% to about 3% by active ingredient weight of vanadyl sulfate; (b) from about 17% to about 62% by active ingredient weight of lipoic acid; (c) from about 36% to about 83% by active ingredient weight of taurine; and (d) from about 0.01% to about 0.04% by active ingredient weight of chromium carnitine.

Preferably, a daily dose (mg/kg-day) of the present composition would be formulated to deliver per kg body weight of the mammal the following active ingredients within the suggested ranges: (a) about 0.005 mg/kg to 15 mg/kg vanadyl sulfate; (b) about 1.0 to 75 mg/kg alpha-lipoic acid; (c) about 5 to 45 mg/kg taurine; and (d) about 0.001 to 0.01 mg/kg chromium carnitine.

The relative amount of the individual components would vary to optimize cost-effectiveness and biochemical synergy. The daily dose may be divided to be consumed as one or more capsules, tablets or softgels one, two or more times per day.

More preferably, the present composition would be formulated to contain the active ingredients in the following proportions: (a) about 3% by active ingredient weight of vanadyl sulfate; (b) about 36% by active ingredient weight of lipoic acid; (c) about 61% by active ingredient weight of taurine; and (d) about 0.04% by active ingredient weight of chromium carnitine.

More preferably, a daily dose (mg ingredient/kg-day) of the present composition would be formulated to deliver per kg body weight of the mammal the following active ingredients; (a) about 3% by active ingredient weight of vanadyl sulfate; (b) about 36% by active ingredient weight of lipoic acid; (c) about 61% by active ingredient weight of taurine; and (d) about 0.04% by active ingredient weight of chromium carnitine.

In preferred embodiments, the composition of this invention further contains a pharmaceutically acceptable carrier As used herein, the term "pharmaceutically acceptable carrier" is meant to include one or more pharmaceutically suitable, inactive excipients, carriers, diluents, lubricants, adjuvants, and lubricants. Non-limiting examples of inactive excipients, carriers, diluents, lubricants, and adjuvants that can be used in the composition of the present invention include: cellulose, calcium carbonate, dicalcium phosphate, starches, lactose, modified food starches, dextrose, calcium sulfate, magnesium carbonate, magnesium stearate, stearic acid, glycerin, vegetable oils, polysorbates, lecithin, silicium dioxide, food glare, talc, croscarmellose sodium, povidone, water and geletin. Additional inactive excipients, carriers diluents, lubricants and adjuvants that may be used with the active ingredient composition of this invention are disclosed in the Handbook of Food Additives (CRC Press), which is incorporated by reference herein in relevant part.

As used herein, the term "lipoprotein" such as VLDL, LDL and HDL, refers to a group of proteins found in the serum, plasma and lymph, which are important for lipid transport. The chemical composition of each lipoprotein differs in that the HDL has a higher proportion of protein versus lipid, whereas the VLDL has a lower proportion of protein versus lipid.

As used herein, the term "triglyceride" means a lipid or neutral fat consisting of glycerol combined with three fatty acid molecules.

As used herein the term "obesity" means a body mass index (BMI) greater than that used to describe a healthy individual as defined by the NIH/WHO BMI Guidelines, which is incorporated by reference herein in relevant part.

As used herein the term "insulin-like activity" refers to the role of insulin in the cellular utilization of glucose, protein and fat resulting in increased protein synthesis, decreased serum lipoproteins and maintenance of normal body weight.

The pharmaceutically acceptable carrier can be present in any conventional amount used in an orally administered composition.

The present invention also provides a method for normalizing insulin action in animals, preferably humans. The method of this invention involves the steps of: (a) providing the composition of this invention; and (b) orally administering the composition to the animal in an amount and for a time period effective to normalize the action of insulin in the animal.

The orally administered composition of this invention can be in any conventional form including, e.g. capsules (hard or soft), tablets, elixirs, powders, granules, suspensions in water or non-aqueous media, sachets, etc. Most preferably, the composition is in the form of one or more tablets, pills or capsules.

If in a tablet, pill or capsule form, the composition of this invention is preferably orally ingested with a liquid, preferably water, more preferably with about eight ounces of water.

Since many modifications, variations and changes in detail can be made to the described preferred embodiment of the invention, it is intended that all matters in the foregoing description and the following examples are interpreted to illustrate and not in any way to limit the invention.

EXAMPLE 1

The most preferred composition of the dietary supplement administered in the method of this invention would supply the following amounts of active ingredients per kg body weight per day: (a) 0.4 mg vanadyl sulfate/kg body weight; (b) 5.0 mg alpha-lipoic acid/kg body weight; (c) 8.5 mg taurine/kg and (d) 0.005 mg chromium carnitine/kg. Improvement in glucose utilization in the diabetic state would be expected to occur following one to two doses. Additionally, the formulation may be used to support or normalize serum triglyceride or lipoprotein levels in diabetic or non-diabetic subjects. This result would be expected in all mammals within one to two weeks.

Additionally, the composition may be used to normalize the body weight of obese animals. Weight loss would be expected following four to seven days of continuous daily administration of the composition and continue until normal body weight or body mass index is achieved. Further dosing following the normalization of body weight is necessary to maintain normal body weight or body mass index.

The composition of this invention is preferably orally administered daily for an indefinite period to maintain continued normalization of insulin actions. Set forth in the tables below are preferred embodiments of the orally administered composition (excluding inactive ingredients) of this invention. The amounts recited in the tables represent the preferred daily dosing (Table 1) of the ingredients listed on a mg ingredient per kg body weight basis. Table 2 describes the range of preferred daily dosing.

TABLE 1

Preferred embodiment of the orally administered composition (excluding inactive ingredient) representing the minimum and maximum daily dose (mg/kg) of this invention

| INGREDIENT | DAILY DOSE [mg/kg] |
| --- | --- |
| Vanadyl sulfate | 0.4 |
| Alpha-lipoic acid | 5.0 |
| Taurine | 8.5 |
| Chromium carnitine | 0.005 |

In preferred embodiments of the soft gel capsule forms of the present invention, the capsule is composed of gelatin, vegetable glycerin, purified water and carob.

For oral administration of the above-recited formulation, the two softgel capsules (together constituting one serving) are preferably taken daily, with eight ounces of water.

TABLE 2

Preferred embodiment of the orally administered composition (excluding inactive ingredient) representing the minimum and maximum daily dose of this invention

| INGREDIENT | DAILY DOSE MINIUM [mg/kg/day] | DAILY DOSE MAXIMUM [mg/kg/day] |
| --- | --- | --- |
| Vanadyl sulfate | 0.005 | 1.5 |
| Alpha-lipoic acid | 1.0 | 75 |
| Taurine | 5.0 | 45 |
| Chromium carnitine | 0.001 | 0.01 |

Thus, there has been disclosed a composition comprising vanadyl sulfate, alpha-lipoic acid, taurine and chromium carnitine and a method for the administration of the composition to normalize the action of insulin in animals. It will be readily apparent to those skilled in the art that various changes and modifications of an obvious nature may be made without departing from the spirit of the invention, and all such changes and modifications are considered to fall within the scope of the invention as defined by the appended claims. Such obvious changes and modifications would include, but not be limited to, the incipient ingredients added to affect the capsule tablet, snack bar or powder manufacturing processes as well as the addition of vitamins, nutrients and herbs.

What is claimed is:

1. An orally administered composition capable of insulin-like activity in animals, comprising: a therapeutically effective amount of vanadyl sulfate, alpha-lipoic acid, taurine, and chromium carnitine.

2. A composition designed to deliver per kg body weight per day the following components:
   a. about 0.005 mg/kg to about 1.5 mg/kg vanadyl sulfate;
   b. about 1.0 to about 75 mg/kg alpha-lipoic acid;
   c. about 5 to about 45 mg/kg taurine; and
   d. about 0.001 mg/kg to about 10 $\mu$g/kg chromium carnitine.

3. A composition designed to deliver per kg body weight per day the following components:
   a. about 0.4 mg/kg vanadyl sulfate;
   b. about 5.0 mg/kg alpha-lipoic acid;
   c. about 8.5 mg/kg taurine; and
   d. about 0.005 mg/kg of chromium carnitine.

4. A composition according to claim 1, comprising:
   a. From about 0.08% to about 3% by active ingredient weight of vanadyl sulfate;
   b. From about 17% to about 62% by active ingredient weight of alpha-lipoic acid;
   c. From about 36% to about 83% by active ingredient weight of taurine; and
   d. From about 0.01% to about 0.04% by active ingredient weight of chromium carnitine.

5. A composition according to claim 1, comprising:
   a. About 3% by active ingredient weight of vanadyl sulfate;
   b. About 36% by active ingredient weight of alpha-lipoic acid;
   c. About 61% by active ingredient weight of taurine; and
   d. About 0.04% by active ingredient weight of chromium carnitine.

6. The composition of any one of claims 1, 2, 3, 4, or 5 wherein said vanadyl sulfate is pharmaceutical grade with a purity of greater than 95% by weight.

7. The composition of any one of claims 1, 2, 3, 4, or 5 wherein said alpha-lipoic acid is pharmaceutical grade with a purity of greater than 95% by weight.

8. The composition of any one of claims 1, 2, 3, 4, or 5 wherein said taurine is pharmaceutical grade with a purity of greater than 95% by weight.

9. The composition of any one of claims 1, 2, 3, 4, or 5 wherein said chromium carnitine is pharmaceutical grade with a purity of greater than 95% by weight.

10. The composition of any one of claims 1, 2, 3, 4, or 5 which further comprises medium chain triglycerides and wherein said medium chain triglycerides are composed of fatty acids chains of 10 to 14 carbons and are pharmaceutical grade with a purity of greater than 95% by weight.

11. The composition of any one of claims 1, 2, 3, 4, or 5 which further comprises added vitamins.

12. The composition of any one of claims 1, 2, 3, 4, or 5 which further comprises added essential minerals.

13. The composition of any one of claims 1, 2, 3, 4, or 5 which further comprises added proteins.

14. The composition of any one of claims 1, 2, 3, 4, or 5 which further comprises additional fats.

15. The composition of ally one of claims 1, 2, 3, 4, or 5 which further comprises added carbohydrates.

16. The composition of any one of claims 1, 2, 3, 4, or 5 which further comprises added flavoring agents.

17. The composition of any one of claims 1, 2, 3, 4, or 5 which further comprises powdered herbs.

18. The composition of any one of claims 1, 2, 3, 4, or 5 which further comprises an extract of herbs.

19. The composition of any one of claims 1, 2, 3, 4, or 5 which further comprises an extract of plants.

20. The composition of any one of claims 1, 2, 3, 4, or 5 which further comprises an extract of microorganisms.

21. The composition of any one of claims 1, 2, 3, 4, or 5 which further comprises a pharmaceutically acceptable carrier.

22. The composition of any one of claims 1, 2, 3, 4, or 5 in any one of the, following forms: tablet, capsule, powder, liquid suspension, chewable bar, or a component of food.

* * * * *